United States Patent
Overwijk

(10) Patent No.: US 6,690,009 B1
(45) Date of Patent: Feb. 10, 2004

(54) METHOD OF DETERMINING THE CHARGE CARRIER CONCENTRATION IN MATERIALS, NOTABLY SEMICONDUCTORS

(75) Inventor: Mark Hubert Frederik Overwijk, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 253 days.

(21) Appl. No.: 09/689,060

(22) Filed: Oct. 12, 2000

(30) Foreign Application Priority Data

Oct. 15, 1999 (EP) .............................. 99203393

(51) Int. Cl.$^7$ .............................................. H01L 21/66
(52) U.S. Cl. ..................... 250/307; 250/310; 250/311
(58) Field of Search ................................. 250/307, 310, 250/311, 306

(56) References Cited

U.S. PATENT DOCUMENTS

| | | | |
|---|---|---|---|
| 5,502,787 A | * 3/1996 | Capasso et al. | 385/123 |
| 5,625,729 A | * 4/1997 | Brown | 385/31 |
| 5,900,633 A | * 5/1999 | Solomon et al. | 250/339.08 |
| 6,118,533 A | * 9/2000 | Banet et al. | 356/450 |
| 6,153,444 A | * 11/2000 | Nakano et al. | 438/14 |
| 6,323,951 B1 | * 11/2001 | Borden et al. | 356/502 |

FOREIGN PATENT DOCUMENTS

| | | | |
|---|---|---|---|
| EP | 0409209 A2 | 7/1990 | H01J/37/252 |
| WO | WO9412680 | 6/1994 | C23C/14/06 |

OTHER PUBLICATIONS

Patent Abstracts of Japan. Publication No. 63271949. Publication Date: 09/11/888. Application Date: Apr. 28, 1987. Application No. 62105125. Applicant: Matsushita Electric Ind Co Ltd; Int.Cl. HO1L 21/66 GO1N 23/225 HO1J 37/28 Method of Semiconductor Analysis.

"Numerical Recipes in Fortran 77", by Press et al, vol. 1, pp. 650–673.

Japanese Public Disclosure 63–271949, Nov. 9, 1988, Matsushita Electr. Ind. Co., Ltd.

* cited by examiner

Primary Examiner—John R. Lee
Assistant Examiner—Anthony Quash

(57) ABSTRACT

A method for determining the concentration of charge carriers in doped specimens, notably semiconductors, wherein the beam produced by an electron source is made to interact with the specimen, an energy spectrum of the electrons in the beam being derived by means of an energy spectrometer. Plasmon frequencies in the specimen are derived by analysis of the spectrum and the concentration of charge carriers in the doped material is derived from said plasmon frequencies.

15 Claims, 3 Drawing Sheets

METHOD OF DETERMINING THE CHARGE CARRIER CONCENTRATION IN MATERIALS, NOTABLY SEMICONDUCTORS

FIELD OF THE INVENTION

The invention relates to a method of determining the charge carrier concentration in a doped specimen, notably a semiconductor. The charge carrier concentration for semiconductors is to be understood to mean the electron concentration in the case of n-type semiconductors as well as the hole concentration in the case of p-type semiconductors. Generally speaking, the dope atom concentration in the material follows directly from such a charge carrier concentration.

The invention also relates to an electron beam apparatus for carrying out such a method.

The distribution of dope atoms is of major importance for correct operation of semiconductor elements. The concentration thereof determines the electrical properties of the doped material and the exact distribution thereof co-determines the correct operation of the semiconductor elements. The manufacture of such semiconductor elements involves various process steps which may influence the distribution of the dope atoms, for example thermal treatments. Therefore, it is desirable to have a method of measuring the distribution of the dope atoms so as to check the effect of the process steps; this is desirable not only during the development of the semiconductor elements, but also during critical process steps in their manufacture.

The following problem will be further illustrated on the basis of dope atom distributions in Si (silicon) doped with B (borium), so in a p-type semiconductor material. The present generation of Si semiconductors is so small that a technique such as "secondary ion mass spectroscopy", being renowned for its favorable detection limit, cannot offer the desired lateral resolution. An alternative technique, wherein a Scanning Electron Microscope (SEM) is used to analyze the energy of secondary electrons obtained by bombardment of a specimen (substrate or wafer) by means of electrons and to measure the charge carrier concentration on the basis of the plasmon frequency, is known from JP-A-63/271949. Because the plasmon energy is of the same order of magnitude as that of the secondary electrons, according to the cited publication measurement is performed on the derivative of the energy spectrum, this leads to inadequate accuracy.

SUMMARY OF THE INVENTION

It is an object of the invention to provide a method of accurately determining the charge carrier concentration, notably in the case of semiconductors of very small dimensions. This object is achieved according to the invention in that the method of the kind set forth is characterized in that the electron beam emanating from an electron source is made to interact with the specimen, after which an energy spectrum of the electrons is derived from this beam by means of a spectrometer, said spectrum being analyzed so as to derive therefrom the plasmon frequency in the specimen and the charge carrier concentration of the doped material being derived therefrom. In other words, measurement is performed on the primary electrons. The detection efficiency of primary electrons is many times higher than that of secondary electrons, because they fill a much smaller solid angle. Furthermore, analysis of the spectrum of secondary electrons is significantly more difficult, because the plasmon peaks occurring appear against a strong signal background; the energy of at least the first plasmon peak is of the same order of magnitude as the energy of the secondary electrons. Furthermore, it is difficult to separate secondary electrons of an energy near that of the primary electrons from the primary electrons; this necessitates the use of complex and hence expensive equipment.

The energy spectrum is preferably determined by means of an "Electron Energy Loss Spectroscopy" (EELS) technique. In as far as the electrons do not lose energy in the specimen, they produce a so-called "zero loss peak" in the energy spectrum, whereas the electrons which interact with the specimen and hence lose energy generally exhibit one or more plasmon peaks in the energy spectrum.

For a plasmon peak the maximum energy loss $E_{max}$ derived from the measured energy spectrum can be expressed by the relation:

$$E_{max}=[(E_p)^2-(\Delta E_p/2)^2]^{1/2}$$

wherein $E_p$ represents the plasmon energy and $\Delta E_p$ represents the width of the plasmon peak. Therefrom, the plasmon energy $E_p$ can be determined and, because $E_p$ equals $h/2\pi.\omega_p$, also the plasmon frequency $\omega_p$. The following relation holds approximately for the plasmon frequency $\omega_p$:

$$n = \frac{m\varepsilon_o}{e^2}\omega_p^2$$

wherein m is the mass of an electron, e is the charge thereof, $\varepsilon_o$ is the dielectric constant and n is the charge carrier concentration.

Because in the example involving borium-doped silicon the electron concentration n in the specimen consists mainly of the difference between the silicon valence electron concentration $n_v$ and the borium hole concentration $n_g$, the value n obtained should be corrected by way of the value of $n_v$. Moreover, for example, because in the case of phosphor-doped silicon the electron concentration n in the specimen consists mainly of the sum of the silicon valence electron concentration $n_v$ and the phosphor conductance electron concentration $n_g$, the value n obtained should be corrected by way of the value of $n_v$. These corrections can be determined by calculation or, as is much more accurate, by calibration. Calibration is then performed by applying the method according to the invention to a non-doped specimen or a non-doped part of a doped specimen.

It has been found in practice that the measured plasmon frequency is also dependent on the thickness of the specimen. Therefore, according to the invention the plasmon frequency $\omega_p$ is corrected for the thickness of the specimen. When the (P)EELS spectrum is measured from the "zero loss" peak to the plasmon peak, a measure of the thickness can be calculated from the ratio of the two peak heights. Using this thickness, the plasmon frequency can be transformed to a thickness-independent value. It has been found in practice that a mainly linear relationship exists between the plasmon frequency and the thickness of the specimen for B-doped Si: $\omega_p$=a.thickness+b($n_g$). Therein, "a" is independent of the B concentration $n_g$ within the measuring accuracy, but "b" is dependent thereon. The previously determined thickness of the specimen can then be used to determine the value of "b" from the measured plasmon frequency, and hence also the plasmon frequency for a thickness "zero" or the plasmon frequency for a standard thickness of the specimen.

In order to derive an energy spectrum of the primary electrons, interacting with the atoms in the specimen or not, notably an "Electron Energy Loss Spectroscopy" (EELS) technique is used. Use is preferably made of "Parallel Electron Energy Loss Spectroscopy" (PEELS) wherein the output signals of the spectrometer used are simultaneously read out and hence the zero loss peak and the plasmon peak or peaks are measured simultaneously. It is a drawback of the serial reading out of the output channels of the spectrometer that, when variations in time (for example, of the current or voltage) occur in, for example, the spectrometer, the measured positions of essentially the same plasmon peak may differ.

Even though it is possible to determine the energy spectrum of the primary electron beam after it has entered into interaction with the specimen during reflection (where the beam is incident on the sample at an acute angle), the electron beam preferably is made to interact with the specimen in transmission. According to the invention the plasmon frequency, therefore, is determined in a "Transmission Electron Microscope" (TEM). When the electron beam is focused on the specimen in a TEM, the charge carrier concentration is determined at that area. The spot size is dependent on the degree of (de)focusing. In the case of a comparatively large spot, the mean charge carrier concentration is determined. However, notably for semiconductors it is very important that the local charge carrier concentration can be determined each time across a given spot size. Therefore, the plasmon frequency is preferably determined in a "Scanning Transmission Electron Microscope" (STEM).

When in the case of comparatively thick samples a plurality of plasmon peaks occur which, moreover, considerably overlap, it is particularly difficult to determine the peak magnitude, peak width and peak position. In addition to the fact that the method disclosed in the cited Japanese patent application is not sufficiently accurate for determining the doping concentration in extremely small semiconductors, it has not been realized (probably for this reason) that the doping concentration might be derived from the plasmon frequency. However, it has been found that, notably in the case of borium-doped silicon, an adequately accurate doping concentration can be determined when the measured energy spectrum is analyzed entirely by way of a "fitting" technique wherein the peak position, the peak height and preferably also the peak width of the "zero loss peak" and the plasmon peak or peaks are determined. A fitting technique of this kind is known, for example, from "Press c.s.: Numerical Recipes in Fortran 77, pp. 650 and further". In the case of comparatively thick specimens it will usually be possible to determine a plurality of plasmons and hence observe a plurality of plasmon peaks in the energy spectrum. Even though these peaks strongly overlap, the successive peak intervals provide enough additional information to enable sufficiently accurate analysis of the spectrum. In the case of comparatively thin specimens, the intensity of the plasmon peak is usually so low that the determination of the peak position and hence the plasmon frequency is insufficiently accurate. Therefore, a somewhat thicker specimen is to be preferred; moreover, a thicker specimen is easier to manufacture.

BRIEF DESCRIPTION OF THE DRAWINGS

The invention will be described in detail hereinafter with reference to the accompanying drawing. Therein.

DETAILED DESCRIPTION OF THE PREFERRED EMBODIMENTS

Figure 1:
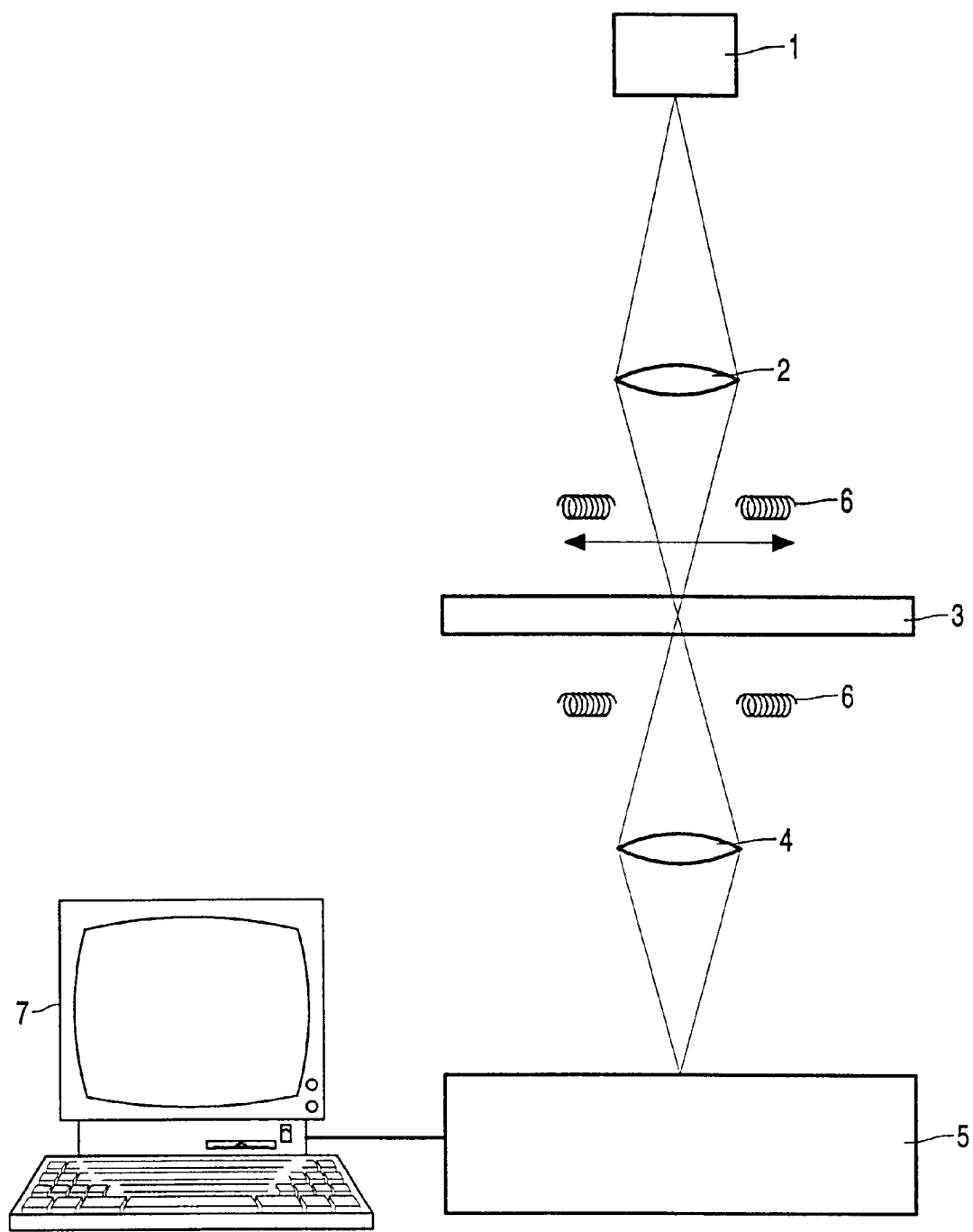
FIG. 1 shows diagrammatically a "Scanning Transmission Electron Microscope" (STEM) whereby an energy spectrum of the electron beam passing through a specimen is obtained.

FIG. 1 shows diagrammatically a STEM which is known per se and includes an electron source 1 which outputs, after acceleration, an electron beam whose electron energy is, for example, of the order of magnitude of from 30 to 1000 keV. Focusing means 2 are provided so as to send this beam in a given location through a specimen 3 doped with given atoms. Part of the electrons will exhibit practically no energy loss; these electrons will exhibit a so-called "zero loss peak" in the energy spectrum. The further electrons will usually give up energy in the form of plasma resonance in the specimen; this is an oscillation of the free electron density and valence electron density which is quantum mechanically described in the formation of a pseudo-particle, called a plasmon, whose energy is determined by the relation $E_p = h/2\pi.\omega_p$, in which $\omega_p$ is the plasmon frequency and h is Planck's constant. It is notably in dependence on the thickness of the sample that one or more plasmon peaks will be visible in the energy spectrum, the energy distances (peak distances) of said plasmon peaks always being substantially the same in conformity with the quantum mechanical description of the plasmons. The width of the plasmon peaks is determined by the relation $\Delta E_p = h/2\pi.\Gamma$, in which $\Gamma$ is the reciprocal value of the relaxation time of the collective oscillation of valence and free electrons upon passage of the beam through the specimen. It has been found that for most semiconductors this plasmon peak lies at an energy loss of the order of magnitude of from 5 to 30 eV.

Figure 2:
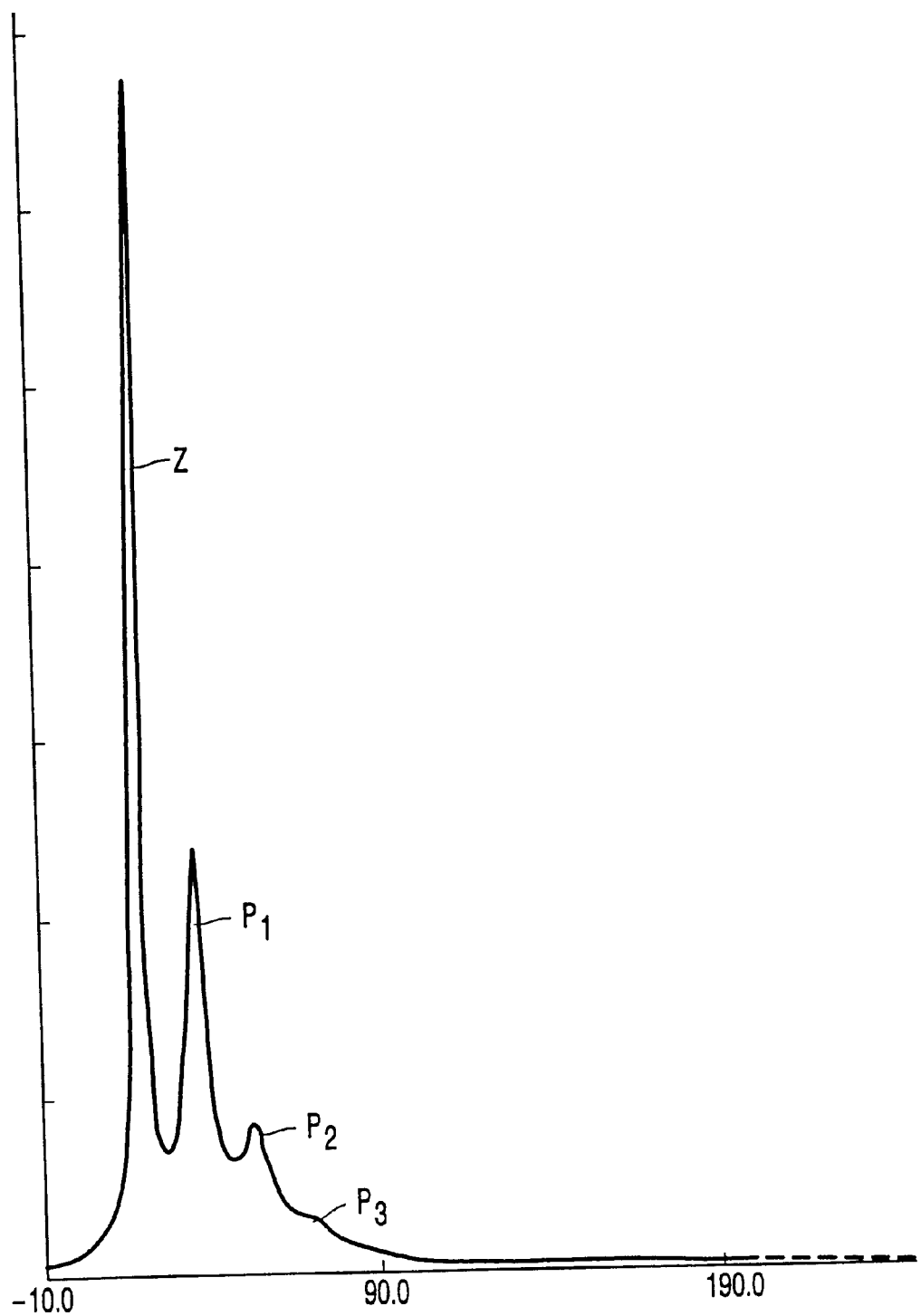
FIG. 2 shows an energy spectrum obtained in the case of a doped Si specimen.

The beam having passed the specimen is conducted to a spectrometer 5 by means of focusing means 4. A variety of known types of spectrometer can be used for this purpose, for example a spectrometer in which the paths of the electrons of different energy are separated from one another in a magnet field. This results in an energy spectrum, for example as shown in FIG. 2 for a P-doped Si specimen. Using processor means 7, notably a personal computer, the associated plasmon frequency $\omega_p$, and therefrom the charge carrier concentration $n_g$, can be determined from the energy spectrum by means of the above-mentioned relations. In FIG. 2 the detected number of electrons is plotted (vertically) in arbitrary units versus the energy loss of the electrons after the passage of the specimen. In addition to the "zero loss peak" z three plasmon peaks $p_1$, $p_2$ and $p_3$ are visible. As has already been stated, the energy spectrum can be analyzed and the plasmon frequency $\omega_p$ determined by means of known "fitting" techniques utilizing the parameters peak amplitude, peak width and peak position, after which, as has already been stated, the charge carrier concentration in the specimen can be determined therefrom and from the charge carrier concentration itself the dope atom concentration of the doped material can be determined. If desired, the plasmon frequency can be corrected, as has already been stated, for the thickness of the specimen.

Because the described method is to be used notably for semiconductors, it is important to determine the charge carrier concentration in both lateral directions of the specimen. Therefore, the STEM shown in FIG. 1 is provided with scanning means 6 for making the electron beam scan the specimen in both lateral directions.

Figure 3:
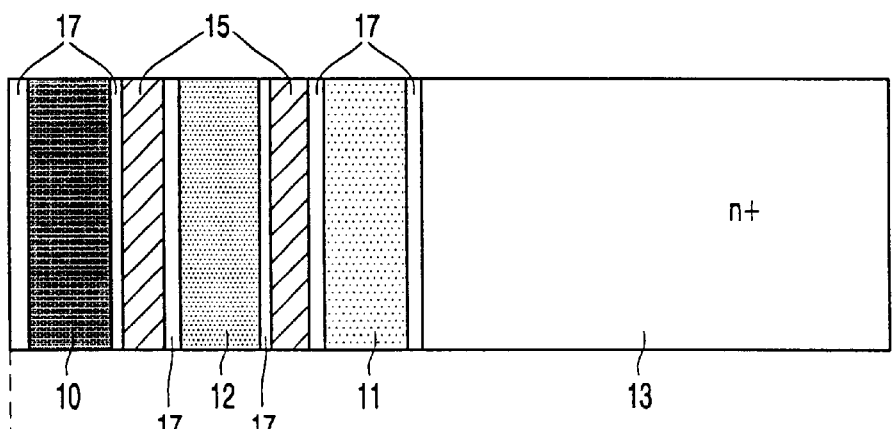
FIG. 3 shows a specimen for test purposes with three B-doped Si layers with an increasing charge carrier concentration, said layers being separated by SiGe layers.

FIG. 3 shows a test specimen with three B-doped Si layers (p-type semiconductor material) 10, 11 and 12. The extreme right layer 13 of the sample is doped with Sb (antimony) (n-type semiconductor material). The three B-doped layers 10 to 12 are isolated from one another by SiGe (silicon germanium) layers 15. Furthermore, Si intermediate layers 17 are provided. The extreme left layer 10 has the highest B concentration (1E19 B/cm$^3$); the extreme right B-doped layer 11 has the lowest B concentration (2E18 B/cm$^3$) and the intermediate B-doped layer 12 has an intermediate B concentration (7.5E18 B/cm$^3$).

Figure 4:
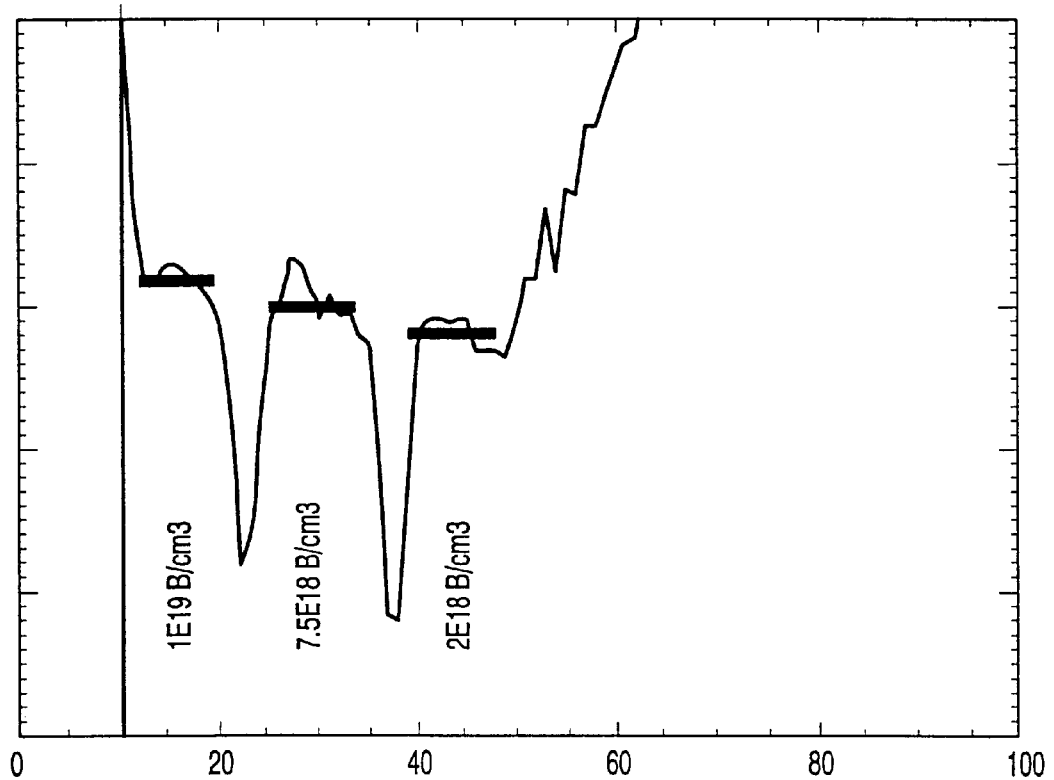
FIG. 4 shows in arbitrary units the charge carrier concentration determined for the layers shown in FIG. 3.

Using this test specimen, the electron concentration in the various layers has been determined by means of the method according to the invention. The results thereof are shown in FIG. 4 in which the electron concentration is plotted (vertically) versus the position of the layers shown in FIG. 3. The heavy line segments represent the mean value of the measured results for the successive layers. It appears from these results that the charge carrier concentration determined from the plasmon energy increases as a function of the dope atom concentration and that, generally speaking, it is, therefore, a measure of the dope ion concentration in a semiconductor material.

The method according to the invention can be used not only for determining the dope atom concentration in semiconductors, but also in, for example, doped isolators. Isolators can be made conductive again to a given extent by doping, notably so as stabilize these isolators in respect of temperature effects.

What is claimed is:

1. A method of determining a charge carrier concentration in a doped portion of a first specimen, said method comprising:

interacting a first electron beam with the doped portion of the first specimen;

measuring a first energy spectrum of primary electrons of the first electron beam involved in the interaction of the first electron beam with the doped portion of the first specimen;

deriving a first plasmon frequency from the first energy spectrum; and deriving the charge carrier concentration from the first plasmon frequency.

2. The method of claim 1, further comprising:

applying a correction to the charge carrier concentration based on a valence electron concentration of the doped portion of the first specimen.

3. The method of claim 2, further comprising:

interacting a second electron beam with a non-doped portion of the first specimen;

measuring a second energy spectrum of primary electrons of the second electron beam involved in the interaction of the second electron beam with the non-doped portion of the fist specimen;

deriving a second plasmon frequency from the second energy spectrum; and determining the correction based on the second plasmon frequency.

4. The method of claim 2, further comprising:

interacting a second electron beam with a non-doped portion of a second specimen;

measuring a second energy spectrum of primary electrons of the second electron beam involved in the interaction of the second electron beam with the non-doped portion of the second specimen;

deriving a second plasmon frequency from the second energy spectrum; and determining the correction based on the second plasmon frequency.

5. The method of claim 1, further comprising:

applying a correction to the plasmon frequency based on a thickness of the doped portion of the first specimen.

6. The method of claim 1, further comprising:

implementing an electron energy loss spectroscopy technique in measuring the first energy spectrum.

7. The method of claim 1, further comprising:

implementing a parallel electron energy loss spectroscopy technique in measuring the first energy spectrum.

8. The method of claim 1, further comprising:

employing a transmission electron microscope in deriving the first plasmon frequency.

9. The method of claim 1, further comprising:

employing a scanning transmission electron microscope in deriving the first plasmon frequency.

10. The method of claim 1, further comprising:

analyzing the first energy spectrum in deriving the first plasmon frequency; and implementing a fitting technique during the analysis of the first energy spectrum.

11. The method of claim 1, further comprising:

determining a peak position of a zero loss peak of the first energy spectrum during the implementation of the fitting technique.

12. The method of claim 10, further comprising:

determining a peak height of a zero loss peak of the first energy spectrum during the implementation of the fitting technique.

13. The method of claim 10, further comprising:

determining a peak width of a zero loss peak of the first energy spectrum during the implementation of the fitting technique.

14. The method of claim 10, further comprising:

determining at least one plasmon peak of the first energy spectrum during the implementation of the fitting technique.

15. An electron beam apparatus for determining a charge carrier concentration in a doped portion of a specimen, said electron beam apparatus comprising:

an electron source operable to emit an electron beam;

a specimen location operable to accommodate a specimen including a doped portion;

a spectrometer operable to measure an energy spectrum of primary electrons of the electron beam involved in an interaction of the electron beam and the doped portion of the specimen; and a processor operable to derive a plasmon frequency from the first energy spectrum, said processor further operable to derive the charge carrier concentration from the plasmon frequency.

* * * * *